United States Patent [19]

Brown et al.

[11] Patent Number: 5,414,164
[45] Date of Patent: May 9, 1995

[54] CHLORINATION PROCESS

[75] Inventors: Stephen M. Brown, Nr Huddersfield; Janet C. Glass, Ilkley; Gary N. Sheldrake, Huddersfield, all of United Kingdom

[73] Assignee: Zeneca Limited Imperial Chemical House, London, United Kingdom

[21] Appl. No.: 101,127

[22] Filed: Aug. 2, 1993

[30] Foreign Application Priority Data

Aug. 3, 1992 [GB] United Kingdom ............... 9216442

[51] Int. Cl.$^6$ .............................................. C07C 17/10
[52] U.S. Cl. ................................................... 570/123
[58] Field of Search ........................................ 570/123

[56] References Cited

U.S. PATENT DOCUMENTS

| 2,469,290 | 5/1949 | Calfee et al. | 570/123 |
|---|---|---|---|
| 3,047,642 | 7/1962 | Wolf | 570/123 |
| 4,060,469 | 11/1977 | Sweeney et al. | |
| 5,120,883 | 6/1992 | Rao et al. | |
| 5,254,771 | 10/1993 | Cremer et al. | |
| 5,315,044 | 5/1994 | Furutaka et al. | 570/123 |

FOREIGN PATENT DOCUMENTS 407990  1/1991  European Pat. Off. .

*Primary Examiner*—Alan Siegel
*Attorney, Agent, or Firm*—Joel G. Ackerman

[57] ABSTRACT

A process for the preparation of 1,1,1-trichlorotrifluoroethane in which 1-chloro-2,2,2-trifluoroethane is subjected to chlorination by bringing the 1-chloro-2,2,2-trifluoroethane into contact with chlorine within a reaction vessel characterized in that the process is conducted in the liquid phase in the presence of a chemical free radical initiator under a pressure of from 1 to 20 bar and at a temperature within the range 50° to 120° C., and the product is separated from the reaction mixture by fractional distillation.

13 Claims, No Drawings

CHLORINATION PROCESS

This invention relates to a chlorination process for the preparation of 1,1,1-trichlorotrifluoroethane. 1,1,1-Trichlorotrifluoroethane is a valuable chemical intermediate which is used, inter alia, in the preparation of precursors of pyrethroid insecticides, such as cyhalothrin anf tefluthrin. Hitherto it has been obtained by various processes including by rearrangement of the isomeric product 1,1,2-trichlorotrifluoroethane in the presence of aluminium halides, and by gas-phase photochemically-initiated chlorination of non-perhalogenated precursors such as 1,1,1-trifluoroethane. However the use of these processes is considered unsatisfactory because of low conversion rates, difficulty in separating the product from the starting material, and/or the formation of undesirable by-products.

It has now been found that by careful selection of the conditions it is possible to obtain 1,1,1-trichlorotrifluoroethane by chlorination of 1-chloro-2,2,2-trifluoroethane, and the process is capable of providing a high degree of conversion with high specificity and easy separation of the desired product. Furthermore it is possible to adapt the process to operate not only on a batch by batch basis but also in a semi-continuous or continuous manner suitable for large scale manufacture of 1,1,1-trichlorotrifluoroethane.

Accordingly the present invention provides a process for the preparation of 1,1,1-trichlorotrifluoroethane in which 1-chloro-2,2,2-trifluoroethane is subjected to chlorination by bringing the 1-chloro-2,2,2-trifluoroethane into contact with chlorine within a reaction vessel characterised in that the process is conducted in the liquid phase in the presence of a chemical free radical initiator under a pressure of from 1 to 20 bar and at a temperature within the range 50° to 120° C., and the product is separated from the reaction mixture by fractional distillation.

In the case of continuous or semi-continuous operation the reactants are continuously fed into the reaction vessel at a rate consistent with the steady state production of 1,1,1-trichlorotrifluoroethane and within a preferred molar ratio of chlorine to 1-chloro-2,2,2-trifluoroethane within the range 1.0 to 2.5. At the steady state the molar ratio of chlorine to total chlorinatable hydrogen atoms is also preferably within the range 0.5 to 1.0.

The process is conducted within a closed system with arrangements to admit the reactants and remove the product. Within the reaction vessel itself the conditions of the process may be controlled by regulation of the rate of addition of the reactants, the reaction temperature and the pressure under which the reaction is conducted. In particular the rates of the potentially competing reactions may be influenced by the choice of temperature and pressure. Pressure is partially dependent on the relative vapour pressure contributions of all the components in the gaseous phase which is in equilibrium with the liquid phase in which the reaction occurs, and may be augmented by introducing pressurised inert gas, for example nitrogen. For optimum conversion the pressure is preferably maintained within the range 5 to 15 bar and more preferably within the range 7 to 13 bar.

The temperature at which the process is conducted is also an important determinant of optimum conversion and is preferably within the range 80° to 110° C.

The process is conducted in the presence of a chemical free-radical initiator intended to catalyse the production of chlorine radicals to promote the chlorination reaction. Suitable free-radical initiators include for example aroyl peroxides such as dibenzoyl peroxide, and azo compounds such as azobisisobutyronitrile, which is particularly preferred. It is preferred that the initiator be present at a constant amount during the process and therfore where continuous operation is used the initiator may be fed continuously at a constant rate in proportion to the continuous addition of the reactants. It is also prefered that the initiator be present in a dissolved form to maximise its effect and to avoid the complications arising from a the presence of a solid phase in the reaction vessel. This is best achieved by dissolving the initiator in a suitable solvent which is either non-reactive or is itself consumed in the process to produce the desired product. Certain non-perhalogenated precursors of 1,1,1-trichlorotrifluoroethane are particularly suitable including 1-chloro-2,2,2-trifluoroethane and 1,1-dichloro-2,2,2-trifluoroethane.

A particularly preferred combination of conditions for conducting the reaction in a continuous manner comprises carrying out the process at a pressure within the range 7 to 13 bar and a temperature within the range 80° to 120° C. in the presence of azobisisobutyronitrile whilst continuously feeding the reactants at a molar ratio of chlorine to 1-chloro-2,2,2-trifluoroethane within the range 1.2 to 1.4.

The product, which is present as a substantial component of the reaction mixture is separated from the other components by a process of fractional distillation. The other components of the reaction mixture are unreacted chlorine, unreacted 1-chloro-2,2,2-trifluoroethane and some 2,2-dichloro-3,3,3-trifluoroethane. After separation these other components can be recycled into the reaction vessel in order to maximise the conversion to the desired product. Fractional distillation provides a simple method of separating the components of the reaction mixture because of the differences in boiling points which are 7° C. for 1-chloro-3,3,3-trifluoroethane, 26° C. for 1,1-dichloro-2,2,2-trifluoroethane and 46° C. for 1,1,1-trichlorotrifluoroethane.

Typically the process is operated by passing a premixed stream of the reactants into the reactor, which may be for example a bubble column chlorinator, into which a solution of the initiator is also being introduced, the rates of addition being controlled so as to allow the contents of the reactor to reach a steady state composition in which product predominates, and to continuously remove the contents, as the product stream, at a rate consistent with the rate of addition of the reactants. Thereafter the product stream is passed into a still and fractionated to obtain the 1,1,1-trichlorotrifluoroethane free from the other components of the stream which are recycled back into the reactant stream.

In the process in which the reactant stream includes recycled components the steady state composition (excluding chlorine) may contain from 45% to 85% by weight of the desired 1,1,1-trichlorotrifluoroethane and less than about 35% by weight of 1,1-dichloro-3,3,3-trifluoroethane, the remainder being unreacted 1-chloro-3,3,3-trifluoroethane. It is an advantage of the process that there is little or no formation of unwanted dimeric or polymeric by-products, and consequently a very high yield with respect to the desired product when recycling is taken into account.

The invention process is illustrated by the following Examples in which the process was conducted in a bubble column chlorinator with a capacity of 950 ml, the center section of which was fitted with a jacket heater and the upper portion, above the liquid level when filled, surrounded by a cooling jacket cooled by circulating butanol at −25° C. The column was connected to a supply of nitrogen under pressure. The components were fed into the bottom of the column at predetermined rates and ratios and the reaction allowed to proceed until a steady state, as shown by sampling the reaction mixture until an unchanging composition (as determined by gas chromatography) was reached. In the examples the reactants and products are designated as follows:

Chlorine—$Cl_2$;
1-chloro-3,3,3-trifluoroethane—CTFE;
1,1-dichloro-3,3,3-trifluoroethane—DCTFE:
1,1,1-trichlorotrifluoroethane—TCTFE.
azobisisbutyronitrile—AIBN (used as 0.2% solution in TCTFE)

EXAMPLE 1

The reactor was filled to the liquid level with a 25/75 by volume mixture of CTFE/TCTFE and pressured up to 120 psig with nitrogen. The contents were heated to 100° C. and the reactants continuously fed in at the following rates:
CTFE 3.0 ml/min
AIBN 1.0 ml/min
$Cl_2$ 800 sccm During the addition the temperature was maintained within the range 90° to 103° C. and the pressure was within the range 120 to 127 psig. A steady state composition (excluding chlorine) was achieved after about 165 minutes, as follows:
TCTFE 64.60%
DCTFE 10.25%
CTFE 24.79%

EXAMPLE 2

The process was conducted as in Example 1. During the addition the the temperature was maintained within the range 90° to 100° C. and the pressure was within the range 115 to 125 psig. A steady state composition (excluding chlorine) was obtained after about 150 minutes, as follows:
TCTFE 67.30%
DCTFE 10.40%
CTFE 22.42%

EXAMPLE 3

The process was conducted in a similar manner to Example 1 except that the feed rates were as follows:
CTFE 1.5 ml/min
AIBN 0.5 ml/min
$Cl_2$ 400 sccm A steady state composition (excluding chlorine) was obtained after about 220 minutes, as follows:
TCTFE 66.42%
DCTFE 10.74%
CTFE 22.65%

EXAMPLE 4

The process was conducted in a similar manner to that described in Example 1 except that a reactor of capacity 300 ml was used and the AIBN was added in the form of a 0.2% solution in a 1:1 (by volume) mixture of DCTFE and TCTFE. The temperature was maintained at 100° C. and the pressure at 127 psig and the feed rates were as follows:
CTFE 0.38 ml/min
AIBN 0.13 ml/min
$Cl_2$ 180 sccm The steady state composition (excluding chlorine) achieved was as follows:
TCTFE 83.6%
DCTFE 9.9%
CTFE 6.4% representing a conversion of CTFE to TCTFE of about 87%.

EXAMPLE 5

In three further experiments using the general procedure of Example 4 mixtures of CTFE, DCTFE and TCTFE were used intended to simulate the effect of recycling the DCTFE. In each case the temperature was within the range 90° to 103° C. and the pressure within the range 120 to 127 psig.
(a) Rate of addition
 CTFE 1.05 g/min
 DCTFE 0.58 g/min
 TCTFE 0.58 g/min
 AIBN 9.23 mg/min
 Steady state composition (excluding chlorine)
 TCTFE 59.93%
 DCTFE 23.52%
 CTFE 16.04%
(b) Rate of addition
 CTFE 0.96 g/min
 DCTFE 0.02 g/min
 TCTFE 1.20 g/min
 AIBN 9.75 mg/min
 Steady state composition (excluding chlorine)
 TCTFE 75.34%
 DCTFE 12.12%
 CTFE 11.98%
(c) Rate of addition
 CTFE 1.06 g/min
 DCTFE 1.17 g/min
 AIBN 4.69 mg/min
 Steady state composition (excluding chlorine)
 TCTFE 48.92%
 DCTFE 33.50%
 CTFE 16.92%

We claim:

1. A process for the preparation of 1,1,1-trichlorotrifluoroethane in which 1-chloro-2,2,2-trifluoroethane is subjected to chlorination by bringing the 1-chloro-2,2,2-trifluoroethane into contact with chlorine within a reaction vessel characterised in that the process is conducted in the liquid phase in the presence of a chemical free radical initiator under a pressure of from 1 to 20 bar and at a temperature within the range 50° to 120° C, and the product is separated from the reaction mixture by fractional distillation.

2. A process according to claim 1 wherein the 1-chloro-2,2,2-trifluoroethane and chlorine are fed continuously to the reaction vessel.

3. A process according to claim 2 wherein the molar ratio of chlorine/1-chloro-2,2,2-trifluoroethane is within the range 1.0 to 2.0.

4. A process according to claim 3 wherein the molar ratio of chlorine to total chlorinatable hydrogen atoms is within the range 0.5 to 1.0.

5. A process according to claim 1 carried out at a pressure within the range 5 to 15 bar.

6. A process acording to claim 1 carried out at a temperature within the range 80°–110° C.

7. A process according to claim 1 in which the chemical free radical initiator is selected from aroyl peroxides and azo compounds.

8. A process according to claim 7 in which the chemical free radical initiator is azobisisobutyronitrile.

9. A process according to claim 2 in which the chemical free radical initiator is continuously fed to the reactor vessel.

10. A process according to claim 9 in which the chemical free radical initiator is used in the form of a solution in a non-perhalogenated solvent.

11. A process according to claim 2 carried out at a pressure within the range 7 to 13 bar and a temperature within the range 80° to 120° C. in the presence of azobisisobutyronitrile, wherein the molar ratio of chlorine/1-chloro-2,2,2-trifluoroethane is within the range 1.0 to 2.0

12. A process according to claim 1 wherein any unreacted 1-chloro-2,2,2-trifluoroethane or non-perhalogenated by-product is collected from the fractionated reaction mixture and recycled into the reaction vessel.

13. A process according to claim 1 wherein any unreacted chlorine is recovered from the fractionated reaction mixture and recycled into the reaction vessel.

* * * * *